United States Patent [19]

Takeuchi et al.

[11] 4,212,664
[45] Jul. 15, 1980

[54] NICOTINAMIDE-AMMONIUM HYDROXIDE PLANT GROWTH REGULATOR COMPOSITIONS

[75] Inventors: Setsuo Takeuchi, Higashiyamato; Akira Kawarada, Tokyo; Yasuo Ota; Masayoshi Nakayama, both of Kounosu, all of Japan

[73] Assignee: Rikagaku Kenkyusho, Wako, Japan

[21] Appl. No.: 22,274

[22] Filed: Mar. 20, 1979

Related U.S. Application Data

[63] Continuation of Ser. No. 785,868, Apr. 7, 1977, abandoned, which is a continuation of Ser. No. 547,204, Feb. 5, 1975, abandoned, which is a continuation of Ser. No. 402,742, Oct. 2, 1973, abandoned.

[30] Foreign Application Priority Data

Oct. 3, 1972 [JP] Japan ................................ 47/99212

[51] Int. Cl.$^2$ ............................................. A01N 5/00
[52] U.S. Cl. .................................................... 71/94
[58] Field of Search ........................................ 71/94

[56] References Cited

PUBLICATIONS

Genkel, Chem. Abst., vol. 73, (1970), 95518w.
Kandaurov, Chem. Abst., vol. 73, (1970), 106423d.
Polimbetova et al., Chem. Abst., vol. 71, (1969), 79992x.
Urbonaire, Chem. Abst., vol. 70, (1969), 76598s.
Chem. Abst., 7th Collective Index, 1650s, entries under ammonium hydroxide.
Chailaknyan, Chem. Abst., vol. 51, (1957), 8906h.
Ovcharov, Chem. Abst., vol. 66, (1967), 84934f.
Epanchinov, Chem. Abst., vol. 77, (1972), 13882ht.

*Primary Examiner*—Catherine L. Mills

[57] ABSTRACT

A plant growth regulator comprising as an active ingredient at least one member selected from the group of nicotinamide and analogues of nicotinic acid.

6 Claims, 4 Drawing Figures

NICOTINAMIDE-AMMONIUM HYDROXIDE PLANT GROWTH REGULATOR COMPOSITIONS

This is a continuation of application Ser. No. 785,868, filed Apr. 7, 1977 which is in turn a continuation of Ser. No. 547,204 filed Feb. 5, 1975, which is a continuation of Ser. No. 402,742 filed Oct. 2, 1973, all abandoned.

BACKGROUND OF THE INVENTION (1) Field of the Invention

This invention relates to a plant growth regulator which, when applied to cereals such as rice and wheat, leguminose crops such as soy bean, red bean and corn and vegetables such as radish, turnip, spinach, cucumber and lettuce, promotes the growth in these plants, and which, when used for treatment of various seeds, promotes germination and rooting in these seeds, and which further has an activity of increasing the chlorophyl content in plants and strengthening the chlorophyl-retaining property in plants.

(2) Description of the Prior Art

Various plant hormones have been known as plant growth regulators and are used in the agricultural field as chemicals for use in artificially regulating the growth in plants. For instance, sodium naphthalene acetate, gibberellins, 2, 4, 5-TP and esrel are broadly known as plant growth regulators of this type.

SUMMARY OF THE INVENTION

This invention provides a novel and useful plant growth regulator comprising as an active ingredient at least one member selected from nicotinic acid derivatives represented by nicotinamide known as a vitamin B complex ($B_5$) and as one component of a coenzyme and related analogues thereof.

Although it has been known that nicotinamide is present in a plant body, it has not been elucidated what function it performs in a plant body. We made extensive research works with view to clarifying this point and found that this substance takes a very important role in biological metabolism of plants. More specifically, we noticed that an unknown organic substance contained in rice chaff has a great contribution of nutrition and growth regulation of rice at the initial stage of germination, and we examined a substance extracted from *Hadsaduri indica* and found that the substance contains said unknown organic compound at a large content. As a result, we confirmed that this substance is nicotinamide. Based on this finding, we have now completed this invention.

Details of the above experiment will now be described. At first, chaff of *Hadsaduri indica* was pulverized by means of a grinder, and the resulting powder was dipped and agitated in a 70% methanol solution to effect extraction. The resulting extract was subjected to silica gel thin layer chromatography by employing a developer comprising 10:2 ratio mixture of isopropanol and 14% aqueous ammonia, to conduct the histogrammatic examination. As a result, it was confirmed that the extracted substance has a conspicuous growth-promoting activity. Therefore, this organic substance was isolated and purified according to the following method.

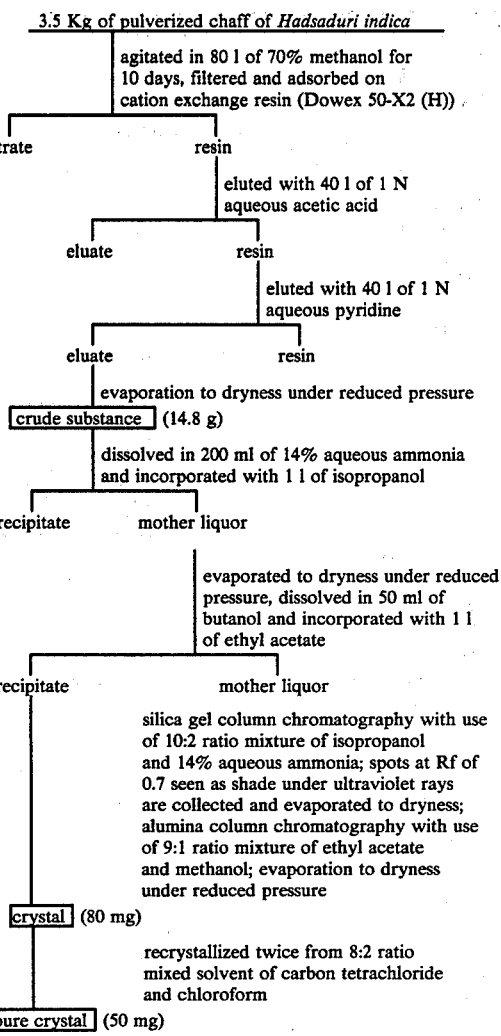

The physical and chemical properties of the so isolated substance are as follows:

Melting point: 130°–131° C.

Crystal form: colorless column

Ultraviolet absorption spectrum (see FIG. 1): 213 m$\mu$ ($E_{1\ cm}^{1\%}=955$), 252 m$\mu$ ($E_{1\ cm}^{1\%}=252$), 257 m$\mu$ ($E_{1\ cm}^{1\%}=397$), 262 m$\mu$ ($E_{1\ cm}^{1\%}=385$)

Infrared absorption spectrum: as shown in FIG. 2

Nuclear magnetic resonance spectrum: as shown in FIG. 3

As a result of the foregoing properties and from the view of the fact that the infrared absorption spectrum of this substance shown in FIG. 2 was quite in agreement with the infrared absorption spectrum of synthesized nicotinamide shown in FIG. 4, this substance was identified to be nicotinamide.

Nicotinamide isolated by the above procedures can, in general, be synthesized with ease according to a known method such as disclosed in the specification of U.S. Pat. No. 2,993,051.

Further, we examined biological activities of the above nicotinamide and the following analogues of nicotinic acid and confirmed that each of them has an excellent plant growth-regulating activity:

(1)  (nicotinic acid)

(2) 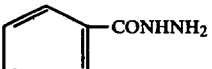 (nicotinic hydrazide)

(3)  (isonicotinic acid)

(4)  (isonicotinamide)

(5) 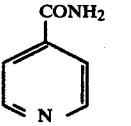 (isonicotinic hydrazide)

(6) 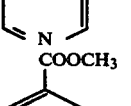 (methyl isonicotinate)

(7) 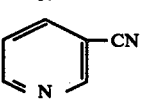 (3-cyanopyridine or nicotinonitrile)

(8) 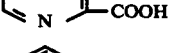 (α-picolinic acid)

(9)  (α-picolinamide)

These analogues of nicotinic acid can readily be synthesized according to known methods. For instance, compound (1) can be synthesized by a method such as disclosed in McElvain, Org. Syn., 4, 49 (1925), compound (2) can be synthesized by a method such as disclosed in Curtius, Nohr. Ber., 31, 2493 (1898), compounds (3), (4) and (6) can be synthesized by a method such as disclosed in Gilmamon & Broadbent, J. Am. Chem. Soc., 70, 2757 (1948), compound (5) can be synthesized by a method such as disclosed in the specification of U.S. Pat. No. 2,830,994, compound (7) can be synthesized by a method such as disclosed in P. G. Teagne & W. A. Short, Org. Syn. Coll., 4, 144 (1963), and compounds (8) and (9) can be synthesized by a method such as disclosed in Mende, Ber., 29, 2887 (1896).

Each of active ingredients of this invention has specific biological activities and exhibits very prominent promoting effects for growth of plants, especially growth at and after the weaning period, adjusting and retaining the chlorophyl content and promoting germination, and the utility of each of the active ingredients has been proven.

Based on the knowledge that the active ingredients of this invention participate in growth of plants in co-operation with the nitrogen component, it has been confirmed that in this invention application of $NH_4^+$ ions is very effective. This is proven by the fact that in the histogram of the above-mentioned crude extract of *Hadsaduri indica*, a prominent effect of promoting the growth, such as illustrated below, is observed when the crude extract is applied together with a 10:2 ratio mixed solvent of isopropanol and 14% aqueous ammonia to aquatic rice (variety: Tangin Bozu).

| Con- | Histogram of Crude Extract Rf. | | | | | | | | | |
|---|---|---|---|---|---|---|---|---|---|---|
| trol | 1 | 2 | 3 | 4 | 5 | 6 | 7 | 8 | 9 | 10 |
| 100 (%) | 100 | 107 | 128 | 100 | 110 | 90 | 131 | 110 | 110 | 114 |

Accordingly, in the practice of this invention, it is desired that the active ingredient is employed in the state mixed with a powdery product obtained by adsorbing $NH_4OH$ on silica gel and drying it, as illustrated in Experiments given hereinafter. However, in the case of certain kinds of seeds, since they contain nitrogen components at high contents at the germination stage and the initial stage of growth, addition of $NH_4OH$ is not particularly necessary at such stage. In order for the active ingredient of this invention to exhibit a growth-promoting effect sufficiently on plants of the so called weaning stage or later stages, it is indispensable that a nitrogen compound should be co-present with the active ingredient of this invention.

Especially, good results have been observed when the active ingredients of this invention are applied to cereals. However, plants that can be treated with the plant growth regulator of this invention are not limited to cereals, but it can be applied effectively to leguminose crops such as soy bean, red bean and corn and vegetables such as radish, turnip, spinach, cucumber and lettuce.

In addition to the effect of promoting the growth in growth in plants, the plant growth regulator of this invention has an effect of promoting the rooting and germination when used for treatment of seeds. Further, when growth plants are immersed in a solution of the active ingredient or when such solution is sprayed directly on grown plants, there is obtained an effect of increasing the chlorophyl content and improving the chlorophyl-retaining property. Accordingly, the plant growth regulator of this invention attains the following advantages.

The harvesting time can be adjusted by accelerating the growing rhythm. Accordingly, it is made possible to shorten or change the cultivation period of crops in cold districts. Further, by increasing the chlorophyl-retaining property, it is made possible to retain freshness for a long time in fresh crops, moreover, since the active ingredients of this invention exhibit effects of heightening the tillering property, growing plant organs (especially leaves), accelerating the chlorophyl synthesis, preventing decomposition of chlorophyl and preventing aging of leaves, the manufacturing efficiency can be highly increased with use of the plant growth regulator of this invention. Therefore, the plant growth regulator of this invention can also be used as a harvest-increasing agent.

Still in addition, since each of the active ingredients of this invention is a composite vitamin, its application causes no environmental pollution and hence, it has characteristics of a pollution-free chemical.

The active ingredient of this invention can be directly applied as it is, and it may be used in the form of a dust, a wettable powder, an emulsifiable liquor or a granule prepared according to an ordinary agricultural chemical preparation method with use of ordinary agricultural additives such as solid or liquid carriers, diluents, extenders and dispersing agents. The plant growth regulator has a very broad effective concentration range, and the concentration can be determined appropriately depending on the intended use.

For instance, in case of dust it can be used at a rate of about 3 Kg per 10 ares, and in case of wettable powder or emulsifiable liquor it can be used by diluting it with water of an amount 5,000 times.

When attainment of other agricultural effects is intended, it is possible to use the plant growth regulator of this invention in combination with other suitable agricultural chemicals such as other plant growth regulators or modifiers, fungicides and insecticides, and fertilizers and the like.

DESCRIPTION OF THE PREFERRED EMBODIMENTS

Figure 1:
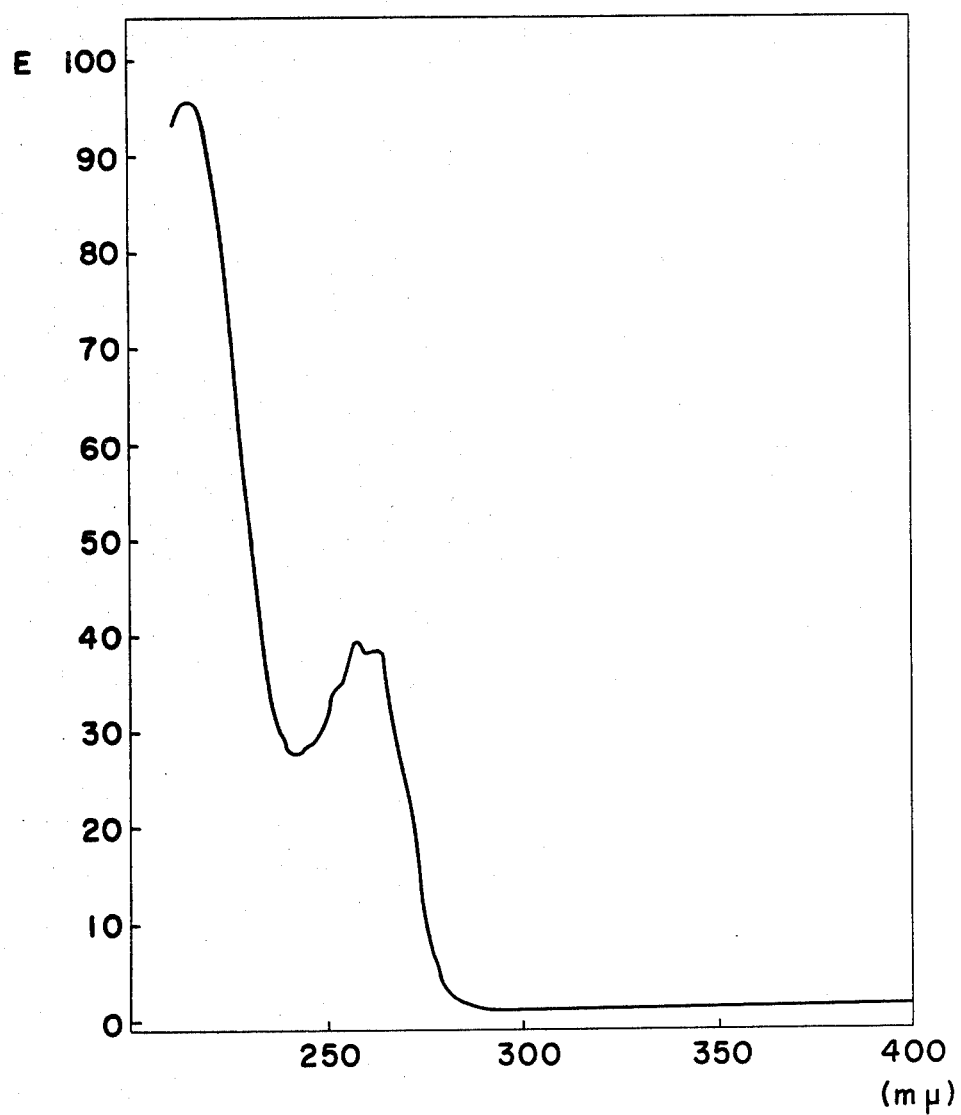
FIG. 1 illustrates the ultraviolet absorption spectrum of nicotinamide isolated from a natural product.
Figure 2:
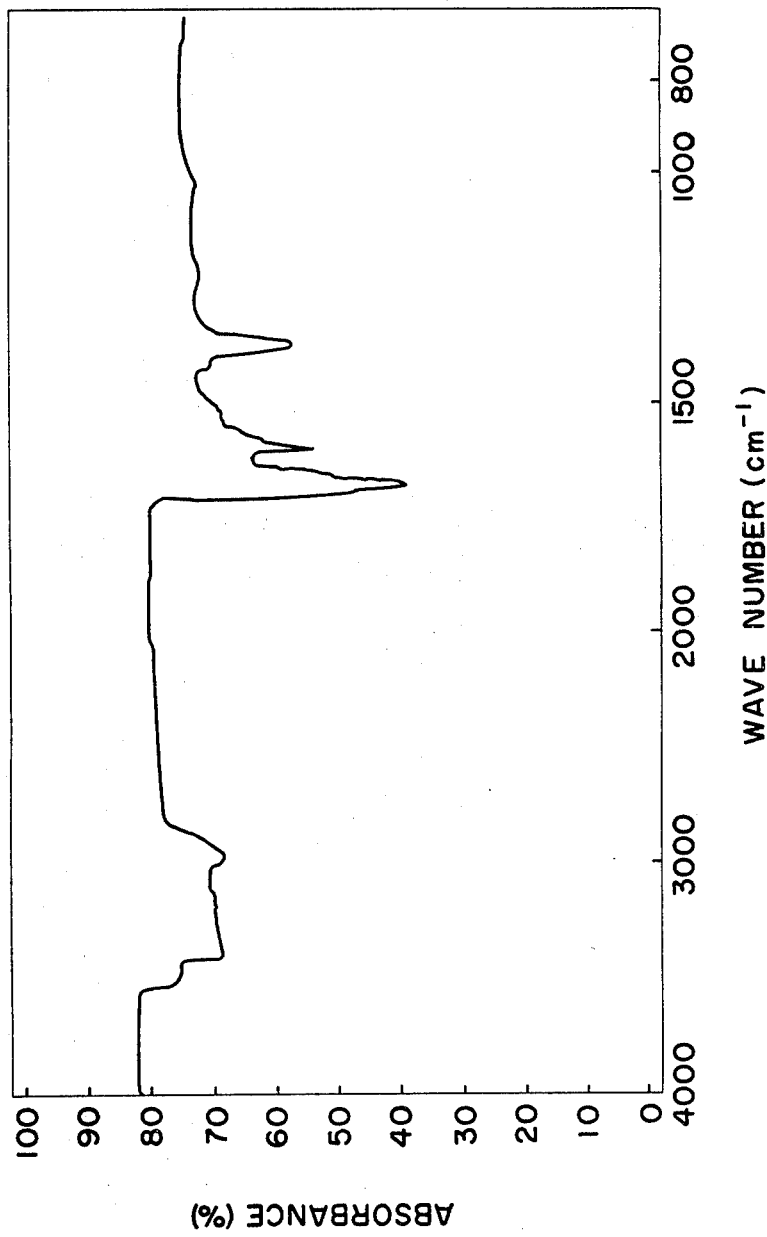
FIG. 2 illustrates the infrared absorption spectrum of the same nicotinamide of FIG. 1.
Figure 3:
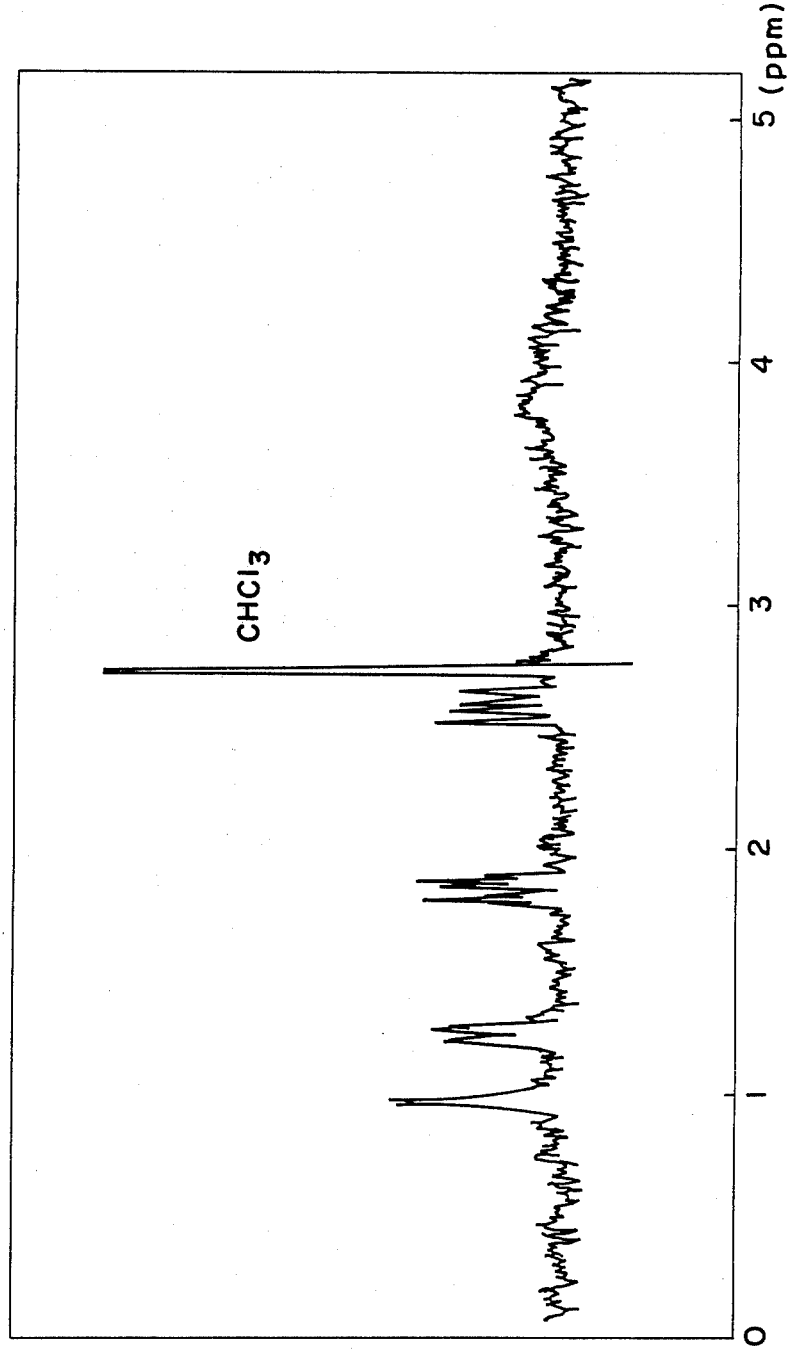
FIG. 3 illustrates the nuclear magnetic resonance spectrum of the same nicotinamide of FIG. 1.
Figure 4:
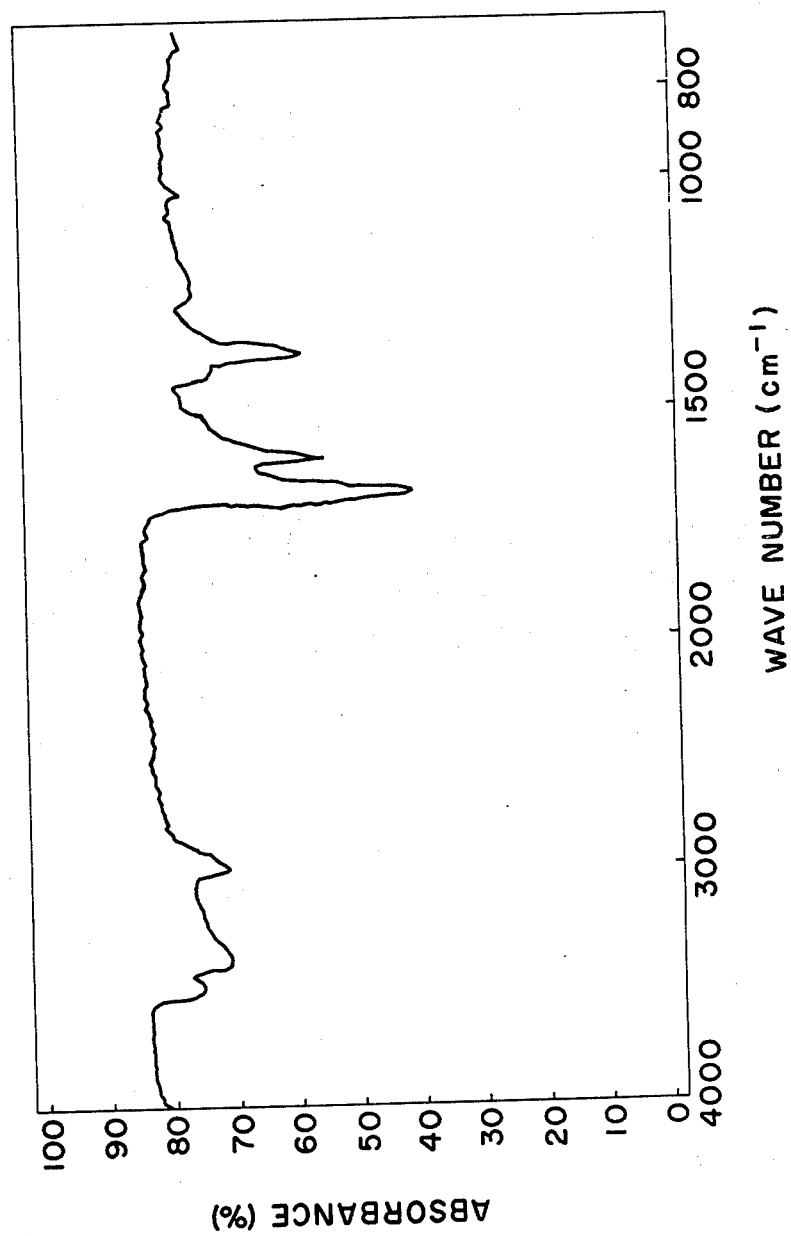
FIG. 4 illustrates the infrared absorption spectrum of synthesized nicotinamide.

Preparation of agricultural chemicals containing the active ingredient of this invention will now be illustrated by reference to Examples, but the scope of this invention is not limited by these Examples. In Examples, all of "parts" are on the weight basis.

EXAMPLE 1

5 parts of nicotinamide was mixed with 95 parts of diatomaceous earth, and the mixture was pulverized to form a dust. The dust was incorporated in soil in an amount of about 3 Kg per 10 ares.

EXAMPLE 2

0.02 part of nicotinamide was mixed with 99.98 parts of diatomaceous earth, and the mixture was pulverized to form a dust. The dust was incorporated in soil in an amount of about 3 Kg per 10 ares.

EXAMPLE 3

2 parts of nicotinic acid, 4 parts of glycol ether and 94 parts of diatomaceous were mixed together, and the mixture was pulverized to form a wettable powder. It was diluted with water of an amount 5,000 times the amount of the powder, and the resulting liquor was sprayed.

EXAMPLE 4

2 parts of isonicotinamide, 4 parts of glycol ether and 94 parts of methanol were mixed together to form an emulsifiable liquor. It was diluted with water of an amount 5,000 times the amount of the liquor. The resulting emulsion was sprayed.

EXAMPLE 5

5 parts of nicotinic hydrazide was mixed with 95 parts of diatomaceous earth, and the mixture was pulverized to form a dust. The dust was incorporated into soil in an amount of about 3 Kg per 10 ares.

EXAMPLE 6

5 parts of isonicotinic acid was mixed with 95 parts of diatomaceous earth, and the mixture was pulverized to form a dust. The dust was incorporated into soil in an amount of about 3 Kg per 10 ares.

EXAMPLE 7

2 parts of isonicotinic hydrazide, 4 parts of glycol ether and 94 parts of methanol were mixed together to form an emulsifiable liquor, which was sprayed in the state diluted with water of an amount 5,000 times the liquor.

EXAMPLE 8

2 parts of methyl isonicotinate, 4 parts of glycol ether and 94 parts of diatomaceous earth were mixed together and the mixture was pulverized to form a wettable powder, which was sprayed in the state diluted with water of an amount 5,000 times the amount of the wettable powder.

EXAMPLE 9

2 parts of 3-cyanopyridine, 4 parts of glycol ether and 94 parts of diatomaceous earth were mixed together and the mixture was pulverized to form a wettable powder, which was sprayed in the state diluted with water of an amount 5,000 times the amount of the powder.

EXAMPLE 10

2 parts of $\alpha$-picolinic acid, 4 parts of glycol ether and 94 parts of methanol were mixed together to form an emulsifiable liquor, which was sprayed in the state diluted with water of an amount 5,000 times the amount of the liquor.

EXAMPLE 11

5 parts of $\alpha$-picolinamide was mixed with 95 parts of diatomaceous earth, and the mixture was pulverized to form a dust, which was incorporated in soil in an amount of about 3 Kg per 10 ares.

Experiments made on plant growth regulators of this invention to evaluate effects on cereals will now be illustrated. Since there is no known chemical to be compared with the active ingredient of this invention, in these Experiments the effects of the active ingredient were evaluated based on the control experiment where no chemical was applied.

Experiment 1

In this Experiment the effect on the grass height of aquatic rice (variety: Tangin Bozu) was examined.

2 mg of powder obtained by adsorbing $NH_4OH$ on silica gel and drying it were charged into each of tubular bottles of a diameter of 2.5 cm, which charged with 2 ml of chemical-free water (control) or an aqueous solution containing nicotinamide at a concentration of 0.001 to 1 ppm. Five seeds were sown in each tubular bottle, and the following results were obtained after 12 days.

Table 1

| | Hulled Rice | | | Unhulled Rice | |
|---|---|---|---|---|---|
| Concentration (ppm) | Height of Plant (cm) | Growth Ratio (%) | Concentration (ppm) | Height of Plant (cm) | Growth Ratio (%) |
| 0 (control) | 3.11 | 100 | 0 (control) | 2.75 | 100 |
| 1 | 3.88 | 124.8 | 1 | 3.82 | 139 |
| 0.1 | 4.46 | 143.4 | 0.1 | 3.98 | 145 |
| 0.01 | 4.12 | 132.5 | 0.01 | 3.63 | 132 |
| 0.001 | 3.60 | 115.8 | 0.001 | 3.40 | 124 |
| 0.0001 | 3.68 | 118.3 | 0.0001 | 3.46 | 126 |

Experiment 2

In this Experiment, the effect on the chlorophyl content of aquatic rice (variety: Tangin Bozu) was examined. With use of chemical-free water (control) and aqueous solutions containing 0.001 to 1 ppm of nicotinamide, seeding and cultivation were conducted under the same conditions as shown in Experiment 1.

After 12 days had passed from seeding, with respect to each test sample, the living body (terrestrial portions of 5 individual bodies) was ground in 7 ml of methanol to extract chlorophyl, and the absorption intensity was determined by spectrophotometer at 666 m$\mu$. Results are shown in Table 2, in which the absorption intensity was expressed in terms of a relative value based on the weight.

Table 2

| | Hulled Rice | | | Unhulled Rice | |
|---|---|---|---|---|---|
| Concentration (ppm) | Chlorophyl Content (absorption intensity) | Relative Chlorophyl Content (%) | Concentration (ppm) | Chlorophyl Content (absorption intensity) | Relative Chlorophyl Content (%) |
| 0 (control) | 3.153 | 100 | 0 (control) | 1.345 | 100 |
| 1 | 3.877 | 123 | 1 | 3.007 | 251 |
| 0.1 | 6.241 | 198 | 0.1 | 3.318 | 255 |
| 0.01 | 3.897 | 123 | 0.01 | 3.190 | 245 |
| 0.001 | 3.635 | 115 | 0.001 | 2.145 | 165 |

In this Experiment, the used chemical was one obtained by diluting nicotinamide with water so that the prescribed concentration (0.001 to 1 ppm) was attained.

Experiment 3

With use of aquatic rice of the same variety as used in Experiment 1, cultivation was conducted according to the water culture method using Kasugai medium. Control medium was incorporated with chemical-free water, and test media were incorporated with aqueous solutions containing nicotinamide at a concentration of 1 or 0.1 ppm. Every 3-4 days, exchange of the culture medium was conducted. After 28 days had passed, the number of stems, the number of leaves, the number of roots, and the body weight were examined to obtain results shown in Table 3.

Table 3

| Concentration (ppm) | Number of Stems (each) | Number of Leaves (each) | Number of Roots (each) | Body Weight (g) | | |
|---|---|---|---|---|---|---|
| | | | | Terrestrial Portion | Subterranean Portion | Whole Body |
| 0 (control) | 2.0 ±0.3 (100) | 7.1 ±0.1 (100) | 22.5 ±1.4 (100) | 0.528 ±0.021 (100) | 0.534 ±0.034 (100) | 1.067 ±0.042 (100) |
| 0.1 | 2.8 ±0.5 (142) | 7.9 ±0.2 (113) | 25.2 ±1.8 (112) | 0.967 ±0.097 (183) | 0.375 ±0.035 (70) | 1.342 ±0.126 (126) |
| 1.0 | 2.8 ±0.2 (142) | 7.9 ±0.1 (113) | 24.7 ±0.7 (110) | 0.910 ±0.035 (175) | 0.363 ±0.013 (68) | 1.263 ±0.032 (118) |

Notes:
(1) Each value was an average value calculated from values of all of tested individuals, and each parenthesized value is the percentage to the control.
(2) The chemical used was one obtained by diluting the emulsifiable liquor formed according to the method described in Example 4 with water so that the prescribed concentration was attained. Also, the emulsifiable liquor not containing the ingredient of this invention was used as a control.

From the results of this Experiment, it was confirmed that application of the plant growth regulator of this invention resulted in 40-50% increase of the stem number, about 10% increase of each of the leaf and root numbers and about 20% increase of the living body weight (especially, 70-80% increase of the terrestrial portion).

Experiment 4

The cultivation was conducted under the same conditions as in Experiment 3 for 28 days. With respect to the main stem, the lamina length and leaf sheath length were measured at each leaf position to obtain results shown in Table 4.

Table 4

| Concentration (ppm) | 2nd Leaf | | 3rd Leaf | | 4th Leaf | | 5th Leaf | | 6th Leaf | | 7th Leaf | | 8th Leaf | |
|---|---|---|---|---|---|---|---|---|---|---|---|---|---|---|
| | Lamina | Leaf Sheath | Lamina | Leaf Sheath | Lamina | Leaf Sheath | Lamina | Leaf Sheath | Lamina | Leaf Sheath | Lamina | Leaf Sheath | Lamina | Leaf Sheath |
| 0 (control) | 9 ±0 (100) | 18 ±1 (100) | 44 ±1 (100) | 35 ±1 (100) | 75 ±2 (100) | 44 ±1 (100) | 88 ±3 (100) | 56 ±3 (100) | 101 ±1 (100) | 75 ±8 (100) | 111 ±1 (100) | 16 ±6 (100) | — | — |
| 0.1 | 10 ±0 (114) | 16 ±2 (86) | 40 ±9 (92) | 33 ±2 (92) | 74 ±5 (98) | 60 ±10 (136) | 98 ±12 (111) | 76 ±8 (136) | 142 ±8 (136) | 98 ±7 (131) | 181 ±15 (130) | 122 ±9 (160) | 280 | 107 |
| 1 | 9 ±0 (100) | 16 ±0 (85) | 42 ±2 (95) | 32 ±1 (92) | 67 ±3 (89) | 41 ±2 (94) | 81 ±3 (96) | 58 ±2 (101) | 121 ±2 (117) | 87 ±3 (116) | 193 ±8 (137) | 116 ±8 (153) | 233 | 89 |

Note:
Each value is an average value (unit: cm) calculated from values of all the tested individuals and the parenthesized value is the percent based on the control.

From the results shown in Table 4, it is seen that the plant growth regulator of this invention exhibits much higher effects of the fifth or higher lamina and the forth or higher sheath, and it is very effective for promoting the growth of plants at and after the weaning stage.

Experiment 5

The state of ears of rice plant cultivated by the same method as in Experiment 3, were examined to obtain the results shown in Table 5.

Table 5

| Concentration (ppm) | Length of Ears (mm) | Average Number of Ears | Number of Seeds |
|---|---|---|---|
| 0 (control) | 111 | 13.0 | 447.2 (100) |
| 0.1 | 111 | 13.0 | 536.9 (120.1) |
| 1.0 | 118 | 15.0 | 628.5 (140.5) |

Note:
The parenthesized value is the percent based on the control.

Experiment 6

In a tubular bottle, germination-forced seeds of aquatic rice (variety: Nipponbare) were cultivated with use of 2 ml of an aqueous solution containing 1 ppm of a nicotinic acid analogue shown in Table 6. Every 3 days, the culture medium was exchanged with fresh one. The cultivation was conducted for 10 days at 30° C. under artificial light of 4,000 lux.

The effects on the second leaf sheath length and yound bud length were examined to obtain results shown in Table 6.

Table 6

| Sample Chemical | Second Leaf Sheath Length (cm) | Young Bud Leaf (cm) |
|---|---|---|
| nicotinic hydrazide | 29.6 | 77.6 |
| isonicotinamide | 32.5 | 77.2 |
| isonicotinic hydrazide | 42.8 | 78.9 |
| 3-cyanopyridine | 42.1 | 81.8 |
| control | 30.4 | 65.3 |

The chemical was used in the form of an emulsifiable liquor prepared according to the method described in Example 4 after dilution of water to a concentration of 1 ppm. Also, the emulsifiable liquor not containing the ingredient of this invention was used as a control. In addition, each of nicotinic acid, isonicotinic acid, methyl isonicotinate, α-picolinic acid and α-picolinamide was formed into an emulsifiable liquor according to the method described in Example 4, diluted with water to 1 ppm and tested in the same manner as above. Results similar to those shown in Table 6 were obtained.

Experiment 7

2-cm square pieces were cut from a developed leaf of aquatic rice at the tiller stage, and they were floated on a sample chemical solution and allowed to stand still in the dark at 30° C. for 4 days. Then, the degree of decomposition of chlorophyl was determined to obtain results shown in Table 7.

Table 7

| Sample Chemical | Control | Concentration (ppm) | | | | |
|---|---|---|---|---|---|---|
| | | 0.1 | 1 | 10 | 100 | 1000 |
| nicotinamide | 0.074 (100) | — | — | — | 0.084 (113) | 0.102 (138) |
| isonicotinamide | 0.074 | — | — | 0.075 | 0.089 | 0.207 |

Table 7-continued

| Sample Chemical | Control | Concentration (ppm) | | | | |
|---|---|---|---|---|---|---|
| | | 0.1 | 1 | 10 | 100 | 1000 |
| | (100) | | | (101) | (120) | (279) |
| isonicotinic hydrazide | 0.074 (100) | — | — | — | 0.075 (101) | 0.101 (136) |
| methyl iso-nicotinate | 0.074 (100) | 0.093 (126) | 0.078 (105) | — | 0.216 (292) | 0.202 (273) |
| 3-cyanopyridine | 0.074 (100) | — | — | — | 0.096 (130) | 0.136 (184) |
| α-picolinamide | 0.074 (100) | — | — | — | 0.129 (174) | 0.153 (207) |

Notes:
(1)Each value is expressed in terms of $O.D._{660}$ determined on the extract formed by extracting 100 mg of the sample plant with 20 ml of 80% ethanol, and the parenthesized value is the percentage based on the control.
(2)Each chemical was formed into an emulsifiable liquor according to the method described in Example 4 and diluted with water to obtain the prescribed concentration (0.1, 1, 10, 100 or 1,000 ppm). Also, the emulsifiable liquor not containing the ingredient of this invention was used as a control.

In addition, each of nicotinic acid, nicotinic hydrazide, isonicotinic acid and α-picolinic acid was formed into an emulsifiable liquor in the same manner as in Example 4 and diluted with water to obtain a prescribed concentration of 0.1 to 1,000 ppm. In thus diluted state, each chemical was used for the same test as described above to obtain results similar to those shown in Table 7.

Experiment 8

Seeds of aquatic rice (variety: Norin No. 29) were collected, and in August next year, they were immersed in an aqueous solution of nicotinic acid (formed into an emulsifiable liquor according to the method described in Example 4 and diluted with water to have a concentration of 1 to 1,000 ppm). Also, the emulsifiable liquor not containing the ingredient of this invention was used as a control. The germination test was conducted at 20° C. to obtain results shown in Table 8.

Table 8

| | Control | Concentration (ppm) | | | |
|---|---|---|---|---|---|
| | | 1 | 10 | 100 | 1000 |
| Germination Ratio (%) (placed in bed for 2 days) | 36 | 74 | 100 | 86 | 92 |

Note:
The employed preparations are the emulsions prepared according to Example 4 and added with water to the dilutions 1, 10, 100 and 1,000.

From the results shown in Table 8, it is seen that nicotinic acid has an activity of promoting germination of aged seeds.

Experiment 9

Aqueous solution of nicotinic acid and nicotinamide (each chemical was formed into an emulsifiable liquor in the same manner as described in Example 4 and diluted with water so as to have a concentration of 1,000 ppm) were applied to aquatic rice (variety: Norin No. 29) at the earing stage and one week after earing. After harvesting, the effects on germination and initial growth were examined to obtain results shown in Table 9.

Table 9

| Sample Chemical | Low Temperature Area bud length (mm) | Low Temperature Area root length (mm) | Medium Temperature Area bud length (mm) | Medium Temperature Area root length (mm) | High Temperature Area bud length (mm) | High Temperature Area root length (mm) |
| --- | --- | --- | --- | --- | --- | --- |
| nicotinic acid | 13.6 (126) | 45.2 (121) | 8.4 (127) | 29.0 (133) | 68 (100) | 56 (85) |
| nicotinamide | 13.5 (115) | 43.3 (115) | 10.4 (158) | 35.4 (162) | 77 (113) | 62 (94) |
| control | 10.8 (100) | 37.5 (100) | 6.6 (100) | 21.8 (100) | 68 (100) | 66 (100) |

Notes:
(1)Low temperature area : maintained at 13° C. for 20 days
Medium temperature area : maintained at 20° C. for 16 days
High temperature area : maintained at 30° C. for 10 days.
(2)In each test, the number of tested individuals was 10 plants and the parenthesized value is the percentage based on the control.
(3)The emulsifiable liquor not containing the ingredient of this invention was used as a control.

Experiments made on plant growth regulators of this invention to evaluate effects on plants other than cereals will now be illustrated. Since there is no known chemical to be compared with the active ingredient of this invention, in these Experiments, the effects of the active ingredient were evaluated based on the control experiment where no chemical was applied.

In these Experiments only chemicals containing nicotinamide as the active ingredient were used. Results similar to those obtained with respect to nicotinamide can be obtained when other analogues of nicotinic acid are employed.

Experiment 10

Nicotinamide was irrigated in an amount of 0, 0.05 or 0.1 g to soil charged in a plastic case having a size of 6 cm × 11 cm × 3 cm, and seeds of lettuce (variety: Warehead) were sown on the soil. 12 days after seeding, nicotinamide was irrigated in the same amount as above. Respective individuals were transplanted on pots (one individual per pot). 8 days after transplantation, the third irrigation of the same amount of nicotinamide was conducted, and 12 days after the third irrigation, the same amount of nicotinamide was irrigated. After one week had passed from the fourth irrigation, the weight of the terrestrial portion and the number of leaves were examined. The results are shown in Table 10.

Table 10

| Amount of Chemical Used at Each Irrigation (g) | Weight (g) of Terrestrial Portion | Percentage to Control | Number of Leaves |
| --- | --- | --- | --- |
| 0 (control) | 0.913 | 100 | 8.3 |
| 0.05 | 1.058 | 116 | 8.5 |
| 0.1 | 1.317 | 144 | 9.0 |

Note:
Each value is a mean value of values obtained with respect to 4 individuals.

Experiment 11

A dust of nicotinamide prepared in the same manner as described in Example 1 in an amount of 0, 1, 5 or 10 g was mixed with soil, and the mixture was packed in a plastic case having a size of 16 cm × 11 cm × 5 cm. Seeds of red bean were sown on the soil and cultivation was conducted for 23 days in a green house. The grass height and the weight of the terrestrial portion were examined to obtain results shown in Table 11.

Table 11

| Amount of Dust (g) | Grass Height (mm) | Percentage to Control | Weight of Terrestrial Portion (g) | Percentage to Control |
| --- | --- | --- | --- | --- |
| 0 (control) | 194 | 100 | 0.96 | 100 |
| 1 | 221 | 114 | 1.19 | 124 |
| 5 | 193 | 99 | 1.24 | 129 |
| 10 | 214 | 110 | 1.18 | 123 |

Note:
Each value is a mean value of values obtained with respect to 10 individuals.

Experiment 12

The test was conducted in the same manner as in Experiment 10 by employing seeds of cucumber (variety: Sagami Hanpaku Setsunari), and the grass height and the weight of the terrestrial portion were examined to obtain results shown in Table 12.

Table 12

| Amount of Dust (g) | Grass Height (mm) | Percentage to Control | Weight of Terrestrial Portion (g) | Percentage to Control |
| --- | --- | --- | --- | --- |
| 0 (control) | 97 | 100 | 1.50 | 100 |
| 1 | 98 | 101 | 1.60 | 107 |
| 10 | 109 | 112 | 1.98 | 132 |

Notes:
(1) The chemical used was a dust prepared in the same manner as described in Example 1. Also, the dust not containing the ingredient of this invention was used as a control.
(2) Each value is a mean value of values obtained with respect to 10 individuals.

Experiment 13

The test was conducted in the same manner as in Experiment 11 by employing seeds of corn (variety: Golden Cross Bandum), and the grass height and the weight of terrestrial portion was examined to obtain results shown in Table 13.

Table 13

| Amount of Dust (g) | Grass Height (mm) | Percentage to Control | Weight of Terrestrial Portion (g) | Percentage to Control |
| --- | --- | --- | --- | --- |
| 0 (control) | 490 | 100 | 3.12 | 100 |
| 1 | 456 | 93 | 3.58 | 115 |
| 5 | 511 | 104 | 3.60 | 115 |
| 10 | 478 | 98 | 3.34 | 107 |

Notes:
The chemical used was a dust prepared according to the method described in Example 1. Also, the dust not containing the ingredient of this invention was used as a control.
(2) Each value was a mean value of values obtained with respect to 10 individuals.

Experiment 14

Seeds of red bean were sown on soil packed in a pot. After 12 days had passed from seeding, a chemical containing nicotinamide at a concentration shown in Table 13 was sprayed in an amount of 100 ml per 3 pots on stems and leaves. After 15 days had passed from chemical application, the grass height and the weight of the terrestrial portion were examined to obtain results shown in Table 14.

Table 14

| Concentration (ppm) | Grass Height (mm) | Percentage to Control | Weight of Terrestrial Portion (g) | Percentage to Control |
| --- | --- | --- | --- | --- |
| 0 (control) | 22.4 | 100 | 1,878 | 100 |

Table 14-continued

| Concentration (ppm) | Grass Height (mm) | Percentage to Control | Weight of Terrestrial Portion (g) | Percentage to Control |
| --- | --- | --- | --- | --- |
| 5 | 24.7 | 110 | 2,095 | 112 |
| 10 | 29.8 | 133 | 2,496 | 133 |
| 20 | 24.7 | 110 | 1,876 | 100 |

Notes:
(1) The chemical used was one formed by preparing an emulsifiable liquor according to the method described in Example 4 and diluting it with water to a prescribed concentration. Also, the emulsifiable liquor not containing the ingredient of this invention was used as a control.
(2) Each value is a mean value of values obtained with respect to 5 individuals.

Experiment 15

Seeds of cucumber (variety: Sagami Hanpaku Setsunari) were sown on soil packed in a pot, and when cucumber grew into a tiller of the one-leaf stage, a chemical containing a prescribed concentration of nicotinamide was sprayed on leaves and stems in an amount of 30 to 40 ml per 4 tillers. After 24 days had passed from chemical application, the grass height and the weight of the terrestrial portion were examined to obtain results shown in Table 15.

Table 15

| Concentration (ppm) | Grass Height (mm) | Percentage to Control | Weight of Terrestrial Portion (g) | Percentage to Control |
| --- | --- | --- | --- | --- |
| 0 (control) | 99.8 | 100 | 2.8 | 100 |
| 0.5 | 102.4 | 102 | 3.2 | 114 |
| 1 | 97.3 | 97 | 3.8 | 136 |
| 5 | 97 | 97 | 4.8 | 171 |
| 10 | 99.5 | 100 | 4.9 | 175 |
| 100 | 104.6 | 105 | 3.5 | 125 |

Notes:
The chemical used was formed by preparing an emulsifiable liquor according to the method described in Example 4 and diluting it with water to a prescribed concentration. Also, the emulsifiable liquor not containing the ingredient of this invention was used as a control.
(2) Each value was a mean value of values obtained with respect to 4 individuals.

What we claim is:

1. A plant growth regulating composition comprising from about 0.005 to about 10% by weight based on the weight of the composition of nicotinamide, a source of $NH_4+$ ions derived from ammonium hydroxide absorbed on silica gel, and an inert carrier therefor.

2. The composition of claim 1, wherein said carrier is selected from the group consisting of diatomaceous earth, glycol ether, methanol, ethanol, clay, kaolin, bentonite, calcium carbonate, nitrocellulose, starch, talc and mixtures thereof.

3. A method for regulating plant growth which comprises applying to plants in the seedling stage or later stages as a growth stimulating compound nicotinamide, and a source of $NH_4+$ ions derived from ammonium hydroxide absorbed on silica gel.

4. The method of claim 3, which comprises simultaneously applying both the growth stimulating compound and the source of $NH_4+$ ions in the form of a composition which includes an inert carrier.

5. The method of claim 4, wherein the composition is applied in an amount of about 3 Kg per ten acres, calculated as a dust.

6. The method of claim 4 wherein the composition is applied by spraying the plants with the composition diluted with water in an amount of about 5,000 times the amount of the liquor calculated as the wettable powder or an emulsifiable liquor.

* * * * *